United States Patent [19]

Gaillard

[11] 4,311,169

[45] Jan. 19, 1982

[54] AIR-WATER MIXER FOR THE ATOMIZER OF A DENTAL HAND PIECE

[75] Inventor: Roger Gaillard, Montferrand le Chateau, France

[73] Assignee: Micro-Mega, S.A., France

[21] Appl. No.: 67,891

[22] Filed: Aug. 20, 1979

[30] Foreign Application Priority Data

Aug. 24, 1978 [FR] France ............................ 78 24972
Jul. 16, 1979 [FR] France ............................ 79 18979

[51] Int. Cl.³ ........................ F16K 11/00; F16K 37/00
[52] U.S. Cl. .............................. 137/556; 137/625.41; 137/625.46; 433/84
[58] Field of Search ............... 433/98, 84; 137/625.41, 137/625.46, 625.17, 556

[56] References Cited

U.S. PATENT DOCUMENTS

| Re. 24,055 | 8/1955 | Daniels | 137/625.46 |
|---|---|---|---|
| 1,240,023 | 9/1917 | Brunk | 137/556 |
| 2,984,008 | 5/1961 | Weisberg | 433/84 |
| 3,057,350 | 10/1962 | Cowley | 137/625.41 |
| 3,445,934 | 5/1969 | Harris | 433/98 |
| 3,661,181 | 5/1972 | Palmer et al. | 137/625.17 |
| 3,674,048 | 7/1972 | Manoogian et al. | 137/625.41 X |

*Primary Examiner*—A. Michael Chambers
*Attorney, Agent, or Firm*—Robert E. Burns; Emmanuel J. Lobato; Bruce L. Adams

[57] ABSTRACT

This air-water mixer for the atomizer of a dental hand piece comprises a body formed with a circular chamber into which open an air supply conduit, a water supply conduit and an outlet conduit for the fluids. One wall of this chamber consists of the inner face of a selector ring mounted for free rotation in the chamber, the inner face of the ring comprising a flat sector adapted to close the inlet port of one and/or the other supply conduits in predetermined positions of the ring, and an inclined sector permitting the free passage of fluid between one and/or the other of the supply conduits and the outlet conduit in other predetermined positions of the ring, this mixer being particularly suited for a dental hand piece provided with an air-water atomizing conduit.

8 Claims, 12 Drawing Figures

AIR-WATER MIXER FOR THE ATOMIZER OF A DENTAL HAND PIECE

FIELD OF THE INVENTION

This invention relates to an air-water mixer for the atomizer of a dental hand piece.

DESCRIPTION OF THE PRIOR ART

Dental hand pieces are known which comprise an air and water output conduit having its outlet directed towards the working area of the dental tool, this conduit leading to an atomizer for cleaning the milled portion while cooling the tool.

When dental hand pieces are not provided with an internal mixing device, the two fluids are mixed as a rule in a Y-shaped member incorporated in the micro motor. However, this system is objectionable in that it precludes any accurate adjustment of the outputs of the two fluids.

SUMMARY OF THE INVENTION

It is the primary object of this invention to avoid this inconvenience by providing an air and water mixer mounted on the micro motor to which the hand piece is secured, or directly on the hand piece proper, between the air and water supply conduits and the mixture outlet conduit.

To this end, the mixer according to this invention, which comprises a body provided with a circular chamber to which an air supply conduit, a water supply conduit and a mixture outlet conduit are connected, a rotary selector ring mounted in said body by means of a central pivot member for adjusting the air and/or water supply input, is characterised in that the inner face of said ring constitutes one of the walls of said chamber, said inner face comprising a flat sector adapted to close the input port of one and/or the other of said supply conduits in predetermined positions of said ring, and a milled sector inclined from the centre outwardly of the ring and so arranged as to provide a free passage between the one and/or the other of said supply conduits, on the one hand, and the outlet conduit, on the other hand, in other predetermined positions of said ring, adequate seals being provided between the various component elements.

Thus, by rotating the rotary ring the dentist can easily and quickly adjust the outputs of the two fluids.

According to another feature characterising this invention, the supply conduits open into the circular chamber through the medium of a pair of tubes of which the inner ends project somewhat into the chamber and are provided with seals engaged by said flat sector of the ring in said predetermined positions of said ring, said flat sector of the ring being parallel to, and somewhat spaced from, the bottom of said chamber.

With this specific form of embodiment, a satisfactory fluidtightness is obtained at the various seals, and the seals projecting from the chamber are not subjected to shearing stress, as frequently observed in prior art constructions, since they are only compressed gradually by said inclined face when the ring is rotated.

According to another feature characterising this invention, the selector ring is provided with a control rod projecting radially from the mixer body. Preferably, the mixer body is secured to an open resilient collar or ring so that it can be detachably secured to the body of the hand piece or of the micro motor to which the hand piece is coupled.

Thus, the dentist can on the one hand adjust very rapidly and easily the mixer operation by moving the control rod, and on the other hand easily fit the mixer for example to the micromotor body to which the hand piece is coupled, said body comprising the corresponding air and water supply conduits.

DESCRIPTION OF THE PREFERRED EMBODIMENTS

Figure 1:
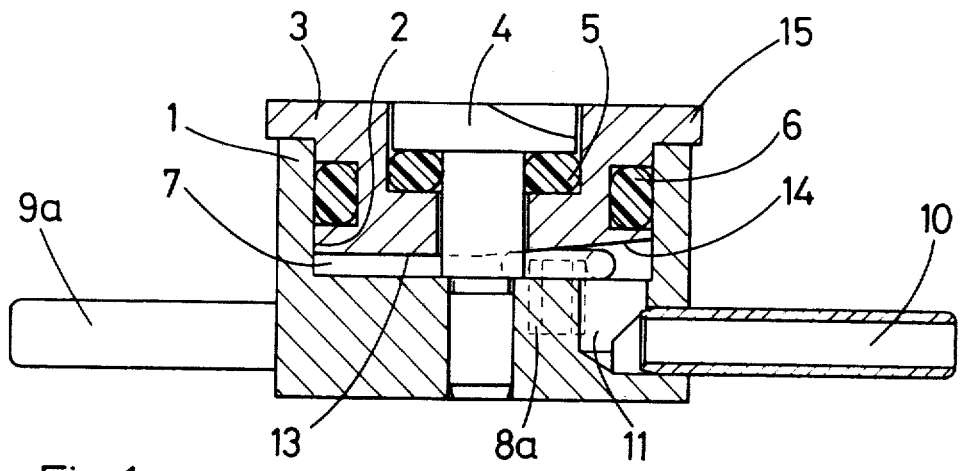
FIG. 1 is an axial section showing diagrammatically a first form of embodiment of the mixer according to the instant invention.
Figure 2:
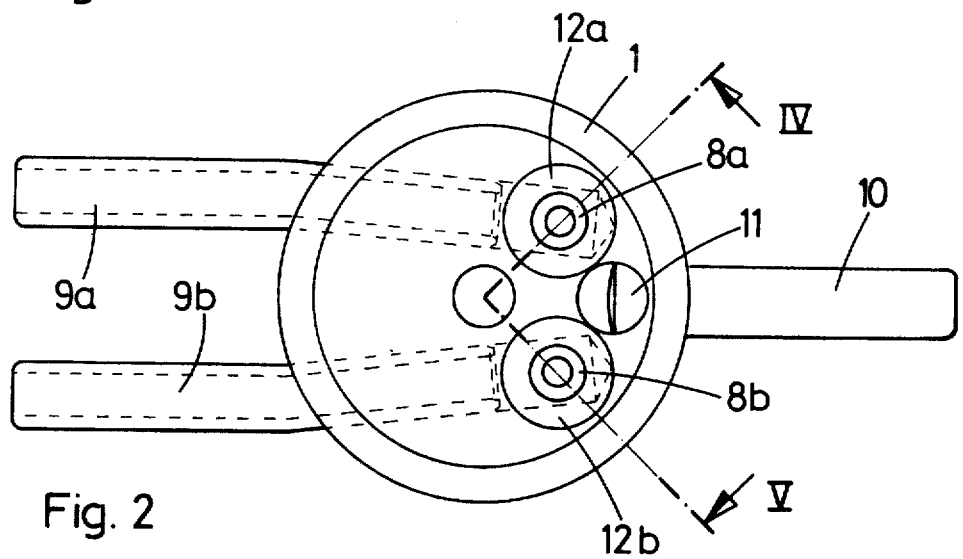
FIG. 2 is a plane view from above of the mixer along, the rotary ring being removed therefrom, according to the first form of embodiment.
Figure 3:
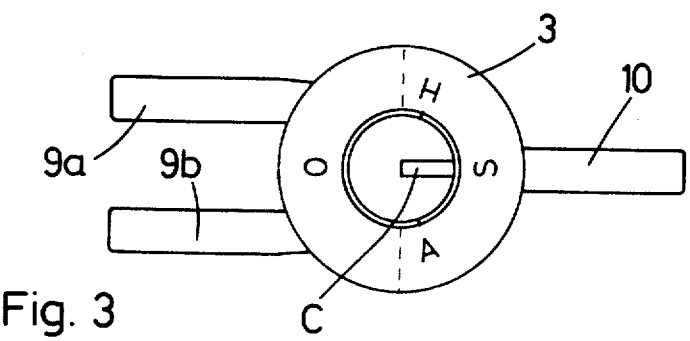
FIG. 3 is a plane view from above of the complete mixer with the various reference marks impressed on the ring, according to the first form of embodiment.

Referring first to FIGS. 1 and 2 of the drawings, the mixer illustrated therein comprises a cylindrical body 1 in which a circular cavity 2 is formed for receiving a selector ring 3 held in position by means of a central pivot member 4 force fitted in said body 1. This selector ring 3 can rotate freely between the pivot member 4 and the body 1, and O-rings 5,6 are provided for sealing the joints between these three elements.

Between the inner face of ring 3 and the bottom of cavity 2 a circular chamber 7 is formed; opening into this chamber through the medium of insert tubes 8a and 8b, respectively, are the air supply conduit 9a and the water supply conduit 9b, respectively, and on the other hand, via a port 11, the outlet conduit 10 for the mixture which is connected in turn to the atomizing nozzle (not shown). The insert tubes 8a, 8b as well as the outlet port 11 open into the bottom of chamber 7 at right angles thereto and the pair of tubes 8a, 8b are so dimensioned and disposed that their inner end project somewhat into the chamber 7, these projecting portions of tubes 8a and 8b being surrounded by corresponding O-rings 12a, 12b, respectively. Furthermore, the two inlet orifices or ports of tubes 8a, 8b and the outlet port are located in a common semi-circular sector of chamber 7, the outlet port 11 being equally spaced from the two inlet ports.

The inner face of selector ring 3 comprises a flat semi-circular sector 13 parallel to the bottom of chamber 7 and the other semi-circular sector 14 is milled or otherwise formed or machined so as to be inclined upwardly and outwardly from the centre to the outer periphery of the ring, as seen in FIG. 1. The flat sector 13 is adapted, in certain predetermined positions of the ring, to engage the O-rings 12a, 12b surrounding the projecting portions of tubes 8a and 8b, so as to seal the inlet port of one and/or the other supply conduits 9a and 9b, and the inclined sector 14 is so arranged as to provide a free passage for the fluids between one and/or the other supply conduits 9a,9b and the outlet conduit 10, in other predetermined positions of selector ring 3.

Besides, the selector ring 3 is provided with an external flange 15 projecting slightly from the outer diameter of the body 1, to facilitate the gripping and turning of this ring.

Reference marks O,A, S and H are impressed on the top or outer surface of selector ring 3 and adapted to be brought in radial alignment with a radial rib or notch C formed in the head of central pivot member 4 so that the practitioner can easily adjust at will the outputs of the air and water mixture.

Figure 4:
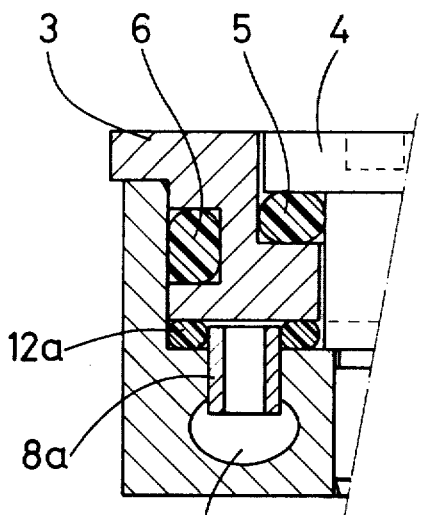
FIG. 4 is a fragmentary section taken along the axis IV of FIG. 2, with the ring in position "O".
Figure 6A:
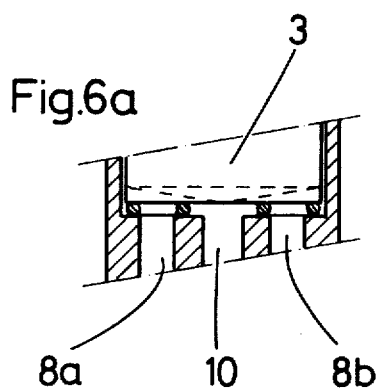
FIGS. 6a to 6d inclusive are diagrammatic sections showing the mixer in four endmost positions of the ring, still according to the first form of embodiment.

The above-described form of embodiment of the mixer according to this invention operates as follows:

When the reference letter "O" of selector ring 3 is brought into radial alignment with the radial mark "C" of central pivot member 4 (FIGS. 4 and 6a), the semicircular flat face 13 of ring 3 overlies the pair of tubes 8a and 8b, thus closing the air and water inlet ports; therefore, no fluid circulation is produced through the outlet conduit 10.

Figure 5:
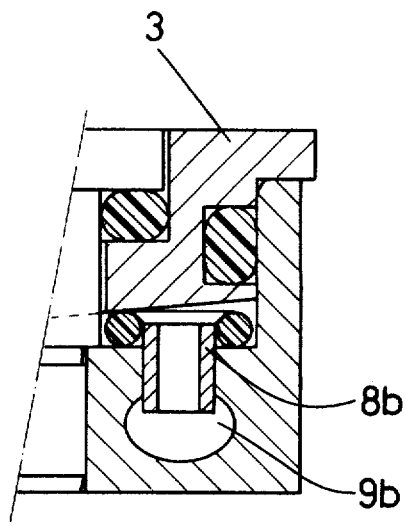
FIG. 5 is a fragmentary section taken along the axis V of FIG. 2, with the ring in position "S".
Figure 6B:
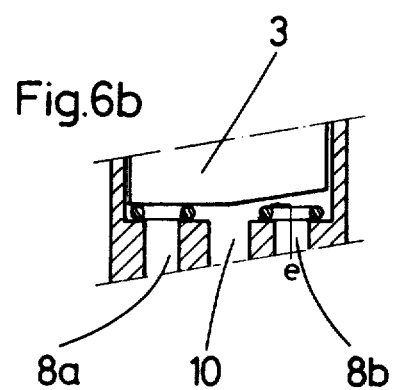
Figure 6C:
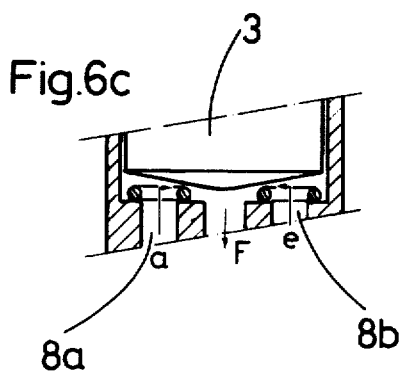

When the reference letter "S" of selector ring 3 is aligned with the radial mark "C" of pivot member 4 (FIGS. 5 and 6c), the inclined face 14 of selector ring 3 overlies the pair of tubes 8a and 8b, so that air and water can flow as shown by the arrows a and e and form a mixture which is subsequently discharged through the outlet conduit 10 as shown by the arrow F.

When the reference letter "H" of selector ring 3 is aligned with the radial mark "C" of pivot member 4 (FIG. 6b), the flat face 13 of ring 3 closes the air inlet conduit 8a while the inclined face 14 permits the flow of water from the water supply conduit 8b to the outlet conduit 10 as shown by the arrow e.

Figure 6D:
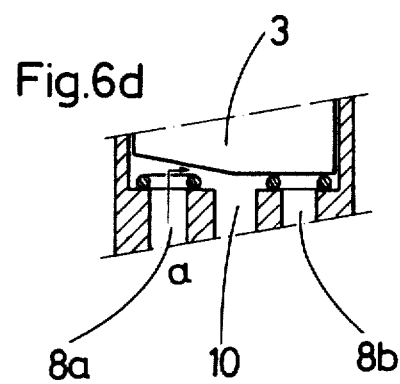

Finally, when the reference letter "A" of selector ring 3 is aligned with the radial mark "C" of pivot member 4 (FIG. 6d), the flat face 13 of ring 3 closes the water supply conduit 8b while the inclined face 14 permits the passage of air from the air supply conduit 8a and the outlet conduit 10, as shown by the arrow a.

According to a preferred form of embodiment of the device of this invention, the reference letters "A" and "H" are disposed on either side of reference letter "S" corresponding to the full opening of the device, and are spaced about 70 degrees from this letter, on either side thereof.

Of course, with this mixer it is possible to obtain different settings for the air and water outputs, for according to the specific angular position given to the selector ring 3 the practitioner can close more or less one of the air and water supply conduits, when it is desired to obtain a mixture in which the fluids are dispensed in different proportions.

Figure 7:
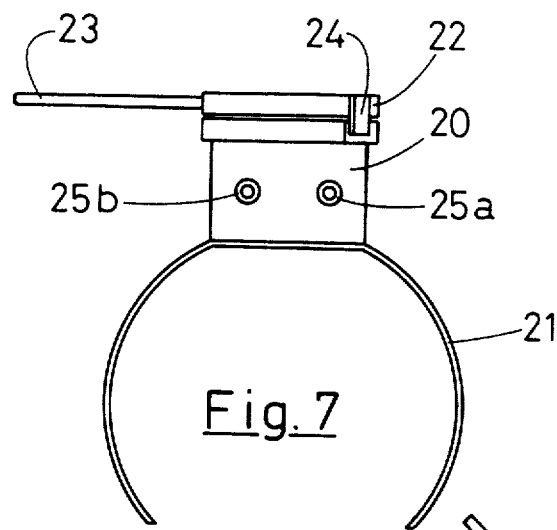
FIG. 7 is an elevational view showing a second form of embodiment of the mixer.
Figure 8:
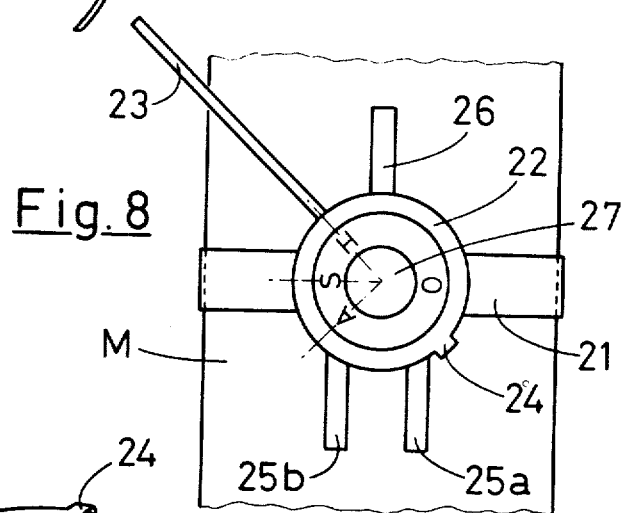
FIG. 8 is a plane view from above showing the mixer of FIG. 7 coupled to a micromotor.
Figure 9:
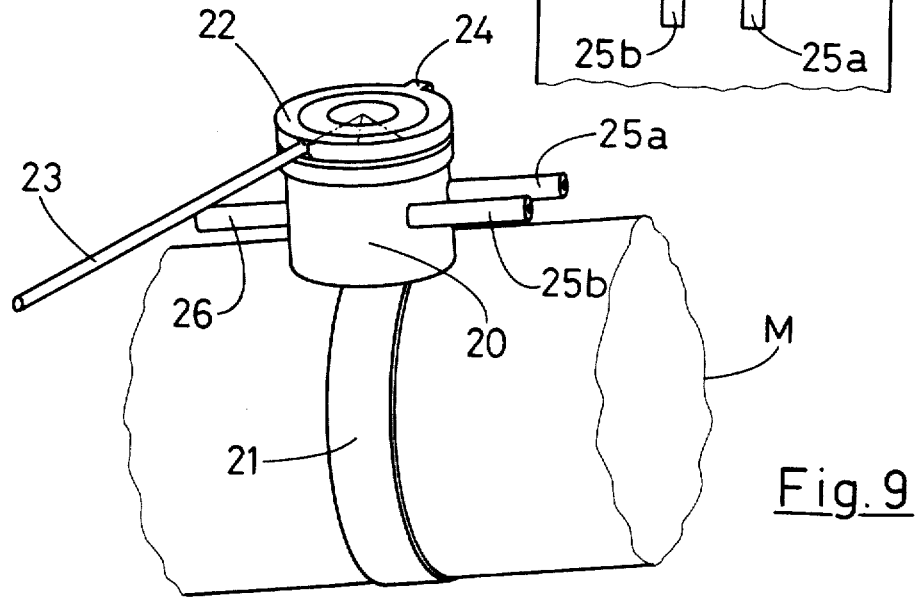
FIG. 9 is a perspective view of this second form of embodiment.

In the modified form of embodiment illustrated in FIGS. 7 to 9 of the drawings, the mixer body 20 is secured to an open resilient collar 21 adapted to detachable clamp the body M of the micro-motor or hand piece, this collar being preferably metallic. Thus, the practitioner can easily fit the mixer to the hand piece and then connect the air and water supply conduit hoses as well as the outlet conduit hose. Likewise, the mixer can be removed very easily and quickly by simply pulling same off the body M, since the two arms of the collar 21 have a certain inherent elasticity.

In these FIGS. 7 to 9 there is also shown a preferred form of embodiment of the selector ring. In this construction, the ring 22 retained by means of the central pivot member 27 is provided with a control rod 23 projecting radially from the mixer body 20 and having a length sufficient to facilitate its actuation by the practitioner's fingers. At a location diametrally opposed to this rod there is also provided a stop 24 adapted to cooperate with a pair of fixed stops formed on the body 20 and spaced to permit a 70-degree angular movement of the ring on either side of the central position "S", thus providing two limit positions for this ring.

According to a preferred version of this specific form of embodiment, the length of control rod 23 exceeds the radius of the micro motor or hand piece body M to which the mixer is to be fitted. Moreover, this mixer is adapted to be so fixed on the micro motor M or hand piece body that the rod 23 projects laterally therefrom, thus affording a better access thereto.

As in the first form of embodiment described hereinabove, the mixer body 20 comprises an air supply conduit 25a, a water supply conduit 25b and an outlet conduit 26 to which the corresponding fluid inlet and outlet conduits or hoses are connected in the conventional manner.

Likewise, reference symbols or letters O,H.S. and A are provided for determining the various operative positions of the mixer.

When utilizing this mixer, the practitioner may adjust the mixer output by holding the latter in his right hand and actuating the control rod 23 projecting radially therefrom either with one finger of the left hand or by using a mirror or any other tool held in his left hand. Therefore, this specific form of embodiment is much more convenient than the first one comprising the selector ring 3, since the adjustment can be made easily and rapidly without depositing the tools held in the hands. The fact of providing two stops for the limit positions will also avoid any loss of time, since it is only necessary to push the rod in one or the other direction until the movable stop 24 engages the corresponding stop carried by the body, so that the practitioner is not required to check the position of the reference marks.

What is claimed is:

1. An air-water mixer for the atomizer of a dental hand piece, which comprises a body provided with a blind bore defining a circular mixing chamber into which open an air supply conduit, a water supply conduit and an outlet conduit, a selector ring rotatably including an inner face mounted in said body and rotatable for adjusting the supply of air and/or water into said chamber, said selector ring inner face defining an upper wall of said chamber, said blind bore and said inner face defining said chamber, said inner face of the ring having a flat sector rotatable to a position to close the inlet port of one and/or the other supply conduits in predetermined angular positions of said selector ring, and a sector on said inner face inclined from the center radially outwardly of said selector ring rotatable to a position to open the passage between one and/or the other supply conduit and the outlet conduit in other predetermined angular positions of said ring, means rotatably mounting said selector ring in said blind bore, and sealing means disposed in said mixer between said ring and said body to maintain the chamber fluidtight.

2. A mixer according to claim 1, wherein said supply conduits open into the bottom of said blind bore and thereby into said circular chamber and comprise a pair of tubes of which the inner ends project somewhat into said chamber, each tube being provided with an O-ring engageable by said flat sector of said selector ring when disposed in positions closing said inlet port of one and-/or the other supply conduits, and said flat sector being parallel to and somewhat spaced from the bottom of said chamber.

3. A mixer according to claim 1, wherein the flat and inclined sectors comprise semicircular portions of the ring and the inlet ports of the two supply conduits and the outlet conduit are disposed under a respective semicircular sector of said ring in said open and closed positions, the outlet conduit being disposed at a same distance from the two inlet ports along the periphery of said body.

4. A mixer according to claim 3, wherein said ring is provided with reference marks disposed to cooperate with a fixed reference sign formed on the means rotatably mounting said selector ring in said blind bore.

5. A mixer according to claim 4, wherein said selector ring is provided with a control rod projecting radially from the mixer body.

6. A mixer according to claim 5, wherein the length of the selector ring control rod is greater than the radius of a body of a handpiece on which the mixer is to be mounted.

7. A mixer according to claim 6, including an open resilient collar secured to said body so that it can be detachably fixed on the body of a handpiece.

8. A mixer according to claim 7, wherein the resilient collar for detachably fixing the mixer to the body is directed parallel to the axis of the handpiece to which the mixer is to be fixed.

* * * * *